United States Patent
Menon (10) Patent No.: US 11,458,308 B2
(45) Date of Patent: Oct. 4, 2022

(54) ELECTRICAL STIMULATION DEVICE FOR IMPROVING FLUIDITY OF MOTION

(71) Applicant: Carlo Menon, Burnaby (CA)

(72) Inventor: Carlo Menon, Burnaby (CA)

(*) Notice: Subject to any disclaimer, the term of this patent is extended or adjusted under 35 U.S.C. 154(b) by 883 days.

(21) Appl. No.: 15/376,653

(22) Filed: Dec. 12, 2016

(65) Prior Publication Data

US 2017/0165481 A1 Jun. 15, 2017

Related U.S. Application Data

(60) Provisional application No. 62/265,894, filed on Dec. 10, 2015.

(51) Int. Cl.
*A61N 1/36* (2006.01)
*A61N 1/04* (2006.01)
*A61N 1/05* (2006.01)

(52) U.S. Cl.
CPC ....... *A61N 1/36003* (2013.01); *A61N 1/0452* (2013.01); *A61N 1/0456* (2013.01); *A61N 1/36031* (2017.08); *A61N 1/36034* (2017.08); *A61N 1/36067* (2013.01); *A61N 1/36139* (2013.01); *A61N 1/0529* (2013.01); *A61N 1/36017* (2013.01); *A61N 1/36025* (2013.01)

(58) Field of Classification Search
CPC ... A61H 1/02; A61N 1/36003; A61N 1/36014
See application file for complete search history.

(56) References Cited

U.S. PATENT DOCUMENTS

| | | | | |
|---|---|---|---|---|
| 6,227,203 | B1 * | 5/2001 | Rise | A61M 5/14276 128/898 |
| 7,110,820 | B2 * | 9/2006 | Tcheng | A61N 1/36067 607/45 |
| 2001/0000187 | A1 * | 4/2001 | Peckham | A61N 1/36003 607/48 |
| 2009/0099627 | A1 * | 4/2009 | Molnar | A61B 5/04014 607/62 |
| 2010/0274304 | A1 * | 10/2010 | Wang | A61B 5/112 607/3 |
| 2011/0288453 | A1 * | 11/2011 | Endo | A61H 1/0244 601/35 |
| 2014/0081346 | A1 * | 3/2014 | Eguibar | A61N 1/36125 607/45 |
| 2014/0180361 | A1 * | 6/2014 | Burdick | A61N 1/0553 607/49 |
| 2017/0136264 | A1 * | 5/2017 | Hyde | G16H 40/63 |

* cited by examiner

*Primary Examiner* — Michael J D'Abreu
(74) *Attorney, Agent, or Firm* — Kafantaris Law Offices; Theo Kafantaris (57) ABSTRACT

The present invention will provide a device in which a movement-impairing episode, such as freezing of gait, is overcome by electrically monitoring and stimulating the individual as soon as the episode is anticipated. The device will be simple and effective when used by individuals suffering from diseases such as Parkinson's Disease without the side effects of oral treatments. This is accomplished through a signal sensing unit, a signal processing unit, a signal generating unit, and an actuation unit.

19 Claims, 8 Drawing Sheets

Sensing system which generates a triggering signal to activate the neuromuscular stimulation to improve motion fluidity.

↓

Unit to process the acquired triggering signal.

↓

Unit to generate high-current neuromuscular stimulation.

↓

Unit to generate high-current neuromuscular stimulation.

ELECTRICAL STIMULATION DEVICE FOR IMPROVING FLUIDITY OF MOTION

CROSS-REFERENCE TO RELATED APPLICATIONS

This application claims the benefit of U.S. Provisional Patent Application No. 62/265,894, filed on Dec. 10, 2015, and incorporated herein by reference.

STATEMENT REGARDING FEDERALLY SPONSORED RESEARCH AND DEVELOPMENT

Not Applicable.

FIELD OF THE INVENTION

This invention relates generally to an electrical stimulation device for improving motion fluidity, and more particularly, to a system and method for electrically stimulating an individual suffering from movement impairing conditions such as freezing of gait.

DISCUSSION OF RELATED ART

Parkinson's Disease is a neurodegenerative disorder that affects the motor system, where brain cells accumulate excessive amounts of alpha-synuclein, causing them to die prematurely. Parkinson's Disease is commonly associated with tremors, stiffness, shaking, difficulty moving, and freezing, as well as other physical and mental effects. Over one million people in the U.S. and up to 10 million worldwide suffer from this disease for which there is no cure and for which the cause is largely unknown. It is considered the world's second most common neurodegenerative disease after Alzheimer's Disease.

Gait can generally be described as the pattern of moving our arms and legs as we move over a solid surface. We select different gaits if we are walking, running, on an inclined/declined surface, or must maneuver around objects. Selecting a gait is a largely subconscious process for most individuals, as we rarely put much thought into the movement of our limbs, the placement of the heel on the ground, the height of our feet as we lift them between steps, or the speed at which our legs and arms move as we carry on throughout the day.

Parkinsonian gait can generally be described as the type of gait exhibited by patients suffering from Parkinson's Disease. Parkinsonian gait is mostly characterized by small shuffling steps and slowness or total loss of movement. Freezing of gait can generally be described as a transient episode lasting less than a few minutes in which gait is halted and the feet cannot be lifted from the ground. Freezing of gait is most common when an individual is turning or just begins to walk, but also when the environment becomes complex and the individual cannot process all of the environmental information. Individuals suffering from Parkinson's disease may exhibit freezing broader than gait, where they cannot continue any rhythmic, repeated movements such as finger-tapping, writing, speech, or blinking of the eyes.

Electroencephalography (EEG) can generally be described as non-invasively monitoring the electrical activity of the brain. EEG measures electrical fluctuations (voltage, current, etc.) resulting from ionic current within the neurons of the brain. Several electrodes are placed on the scalp which record the brain's spontaneous electrical activity, most commonly resulting in a plurality of wave patterns. EEG is effective at diagnosing epilepsy, sleep disorders, comas, tumors, strokes, or brain death. Electromyogram (EMG) is similar to an EEG, but measures electrical impulses within the muscles instead of the brain.

The vestibular system can generally be described as the sensory system that provides us with a sense of balance. Galvanic vestibular stimulation (GVS) is a method of sending a specific electrical stimulus to the vestibular system for manipulating the sense of balance of the individual. GVS systems exist for medical, commercial, and military purposes, but the technology is still in its infancy. Most commonly, electrodes are placed behind the ear and are connected to a controller for manipulating the frequency and intensity of the electrical stimulus sent to the electrodes. A related neurostimulation method is transcranial direct current stimulation (tDCS), where a constant, low level of current is delivered to a specific part of the brain through electrodes on the scalp.

While several treatments exist for improving fluidity of motion such as those suffering from freezing of gait, none are particularly effective and adapted to work on demand. As such, there is a continued need for a device in which movement impairing episodes are overcome by electrically monitoring and stimulating the individual as soon as the episode is anticipated. Furthermore, there is a continued need for a device which is simple and effective in its operation and implementation. The present invention satisfies these needs.

SUMMARY OF THE INVENTION

The present invention will provide a device in which a movement impairing episode is overcome by electrically monitoring and stimulating the individual when the occurrence of the episode is predicted. The present invention will be simple and effective when used by individuals suffering from various diseases including Parkinson's Disease without the side effects of conventional treatments. This is accomplished through a signal sensing unit, a signal processing unit, a signal generating unit, and an actuation unit.

The present invention comprises applying electrical stimulation to improve motion fluidity. Such an electrical stimulation can be applied to the head, either invasively or not invasively, or to other parts of the body, which can be administrated via surface electrodes, needles, or nerve cuffs. The electrical stimulation can also be applied in the proximity of the ear via galvanic vestibular stimulation.

These and other objectives of the present invention will become obvious to those of ordinary skill in the art after reading the following detailed description of the preferred embodiments. It is to be understood that the foregoing general description and the following detailed description are exemplary, and are intended to provide further explanation of the invention as claimed.

DETAILED DESCRIPTION OF THE PREFERRED EMBODIMENT

Illustrative embodiments of the invention are described below. The following explanation provides specific details for a thorough understanding of and enabling description for these embodiments. One skilled in the art will understand that the invention may be practiced without such details. In other instances, well-known structures and functions have not been shown or described in detail to avoid unnecessarily obscuring the description of the embodiments.

Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively. Additionally, the words "herein," "above," "below" and words of similar import, when used in this application, shall refer to this application as a whole and not to any particular portions of this application. When the claims use the word "or" in reference to a list of two or more items, that word covers all of the following interpretations of the word: any of the items in the list, all of the items in the list and any combination of the items in the list.

In the preferred embodiment, the present invention comprises a signal sensing unit 20, a signal processing unit 30, a signal generating unit 40, and an actuation unit 50. The signal sensing unit 20 and the signal processing unit 30 are responsible for detecting and recording the onset of a movement-impairing episode, such as freezing of gait, while the signal generating unit 40 and the actuation unit 50 are responsible for releasing the user from the movement-impairing episode. The signal sensing unit 20 and actuation unit 50 further comprise a plurality of electrodes 21 for receiving and sending electrical stimulation, respectively. These elements work in conjunction to detect and provide electrical stimulation to improve motion fluidity.

The signal sensing unit 20 comprises a means of receiving a signal from the user when movement-impairing episode is anticipated. More specifically, the signal sensing unit 20 is adapted to detect and record electrical stimulation through one or a plurality of electrodes 21, wherein the electrical stimulation may be received involuntarily or voluntarily. This signal will then be transduced into an electrical signal for activating other components of the present invention. Involuntary signals occur automatically once elements of a movement-impairing episode are detected, while voluntary signals comprise manual actions from the user once a movement-impairing episode is anticipated.

In the preferred embodiment, the signal sensing unit 20 will involuntarily detect neuromuscular electrical stimulation originating from the brain that predicts the onset of a movement-impairing episode. Here, neuromuscular electrical stimulation is detected by monitoring for brain activity/inactivity through electroencephalography (EEG), magnetic resonance imaging, magnetoencephalography, near infrared spectroscopy, or other suitable techniques. In this embodiment, electrodes 21 are placed on or in close proximity to the head of the user, wherein the electrodes 21 are capable of detecting brain activity.

In an alternative embodiment, neuromuscular activity is directly detected by monitoring for body activity/inactivity through electromyography (EMG) or force-myography (FMG). In this embodiment, electrodes 21 and/or sensors are placed on or in close proximity to muscles for directly reading neuromuscular signals generated by the brain. Alternatively, neuromuscular activity is indirectly detected by monitoring for body activity/inactivity through an inertial measurement unit comprising eye-trackers, inertial measurement sensors (e.g. accelerometers, gyroscopes, magnetometers, tilt sensors), strain/stretchable sensors (e.g. resistive sensors, capacitive sensors, optical fiber-technologies), revolute sensors (e.g. potentiometers, encoders), cameras, or other suitable techniques.

In a further alternative embodiment, the signal sensing unit 20 will receive a voluntarily signal from the user predicting the onset of a movement-impairing episode. Examples of voluntary signals include pressing a button, waiving a limb, sound activation, clenching of teeth, or other manual triggers suitable for reliably sending a signal to the signal sensing unit 20. In this embodiment, electrodes 21 may or may not be attached to the body. For example, the signal sensing unit 20 is adapted to receive not only manual triggers, but may sense these triggers through EEG, EMG, or other methods, where the manual trigger will also generate an identifiable fingerprint in the readings of the signal sensing unit. Once a manual trigger is detected, the signal generating unit 40 and actuation unit 50 are activated.

The signal processing unit 30 is adapted to receive data from the signal sensing unit 20, process said data, and calculate whether said data predicts the onset of a movement-impairing episode. Depending on the type of sensing above (brain activity, body activity, body movement, voluntary activation), various data ranges are relevant for triggering the activation of the device. For example, when detecting activity through EMG, the range between 50-150 Hz is relevant, while ranges between 3-8 Hz and 16-35 Hz are particularly important for EEG. For clenching, all data above 10 Hz is relevant.

Data processing comprises signal amplification, noise reduction (e.g. low/high pass filters), frequency transformation, wavelet transformation, and signal features extraction such as signal power, wavelength, root-mean-square value, auto-regressive model, principal components, slope, linear fit, non-linear fit, common special filter, and mean absolute value. This data will be compared against predefined threshold values or classification and machine learning schemes comprising supervised, unsupervised, semi-supervised, reinforcement, and deep-learning schemes.

Thresholds or classification schemes discriminate fluid motion versus non-fluid motion, such as freezing, by either evaluating the absolute amplitude of the signals (or their powers) or normalizing such an amplitude to the signal recorded across different other spectral ranges. In one embodiment, data calculation for predicting a movement-impairing episode comprises comparing processed data against predefined threshold values, where values that exceed the threshold amounts indicate a movement-impairing comprises comparing processed data to a classification scheme based on algorithms such as linear discriminant analysis (LDA) or support vector machines (SVM).

The signal generating unit 40 is adapted to receive data from the signal processing unit 30 and generate neuromuscular stimulation, namely, through a current signal delivered by the actuation unit 50. The neuromuscular stimulation can be applied when the user is relaxed before performing an action and/or during motion. In addition, the intensity of the stimulation can be adjusted to the individual's needs. For instance, the intensity can be low intensity and applied for a long period of time or could be of high intensity and applied for short periods. Low and high intensities can also be alternated over time.

The actuation unit 50 is adapted to receive the neuromuscular stimulation generated by the signal generating unit 40 and deliver it to the user. In the preferred embodiment, neuromuscular stimulation is applied to the head (e.g. galvanic vestibular stimulation, electrical brain stimulation, EBS) either invasively (e.g. deep brain stimulation, DBS) or not invasively (e.g. transcranial direct-current stimulation). In an alternative embodiment, the neuromuscular stimulation is applied to other parts of the body (e.g. neuromuscular electrical stimulation, MMES), which can be administrated via surface electrodes, needles, or nerve cuffs. Such an electrical stimulation can also be applied in the proximity of the ear as a wearable device via galvanic vestibular stimulation.

Various output signals can be generated depending on the affected region. For example, a signal between 0.3-3 mA can be used for galvanic vestibular stimulation having a direct current signal, while a signal range between 0.1-50 Hz can be used with an alternating current signal. A signal whose power is inversely proportional to its frequency can also be used, also known as "pink noise." Alternatively, when the affected region is a muscle on the leg, the current can be between 0.1-130 mA with a pulsing waveform having biphasic rectangular impulses, with a pulse width between 20-500 µs and waveform frequency between 1-140 Hz. In an exemplary embodiment, current stimulation is not provided earlier than 30 minutes before a movement-impairing episode, current amount does not exceed 3 mA, and stimulation duration does not exceed 60 minutes.

In a first embodiment, the electrodes 21 used to acquire the signal through the signal sensing unit 20 can be distinct from the electrodes 21 used to provide stimulation through the actuation unit 50. In an alternative embodiment, the same electrodes 21 used to acquire the signal can also be used to provide the stimulation. For instance, a cap can be instrumented to accommodate electrodes 21 for recording EEG and providing electrical stimulation. In a further alternative embodiment, electrodes 21 placed in proximity of the ear and/or in the ear, can be used to either record or stimulate or, alternatively, both record and stimulate. In yet a further alternative embodiment, electrodes 21 placed in the leg can record EMG or provide electrical stimulation or, alternatively, both record and stimulate. The electrodes 21, either those connected to the signal processing unit 30 or the signal generating unit 40, can communicate with their respective components either wirelessly or wired.

Figure 1:
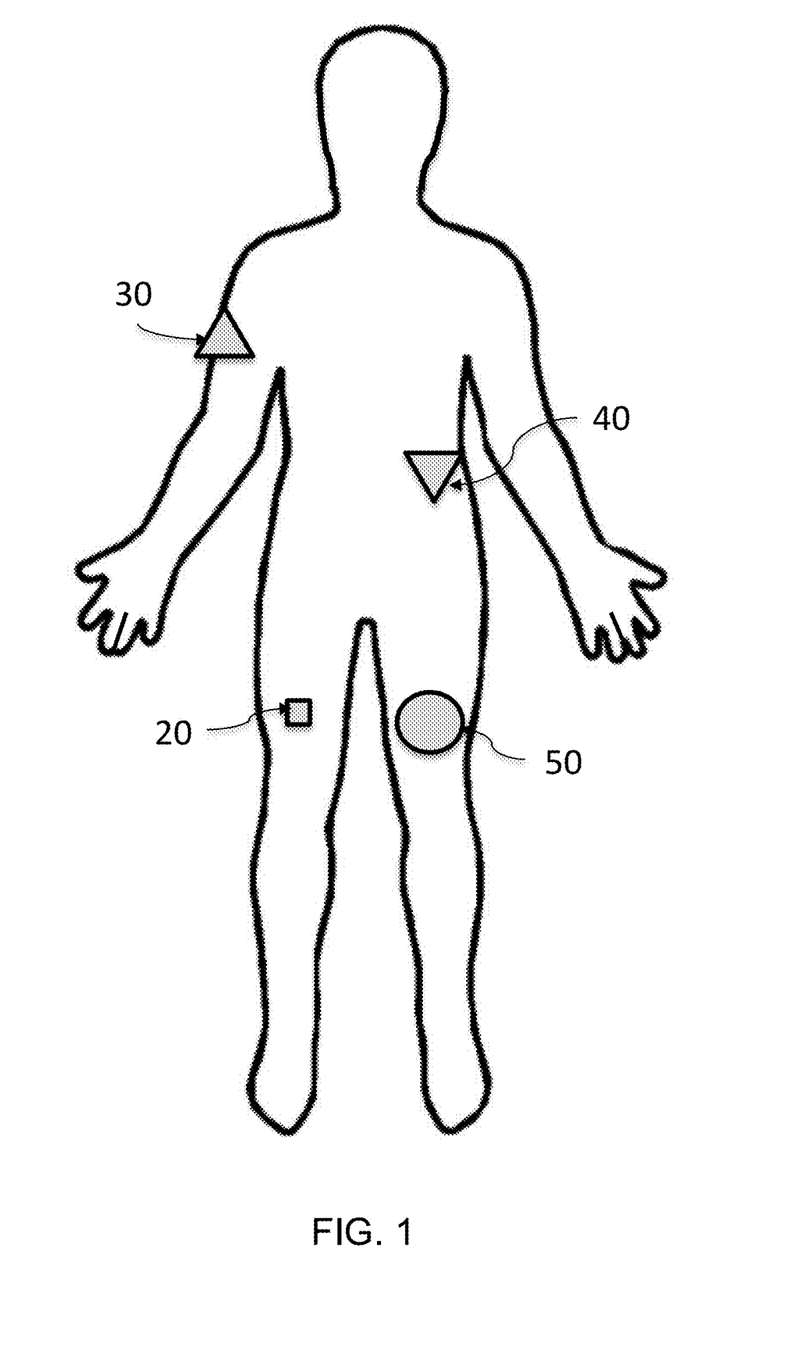
FIG. 1 is a front perspective view of the present invention wherein the signal sensing unit and the actuation unit are positioned near the muscles of the user for neuromuscular detection and stimulation.
Figure 2:
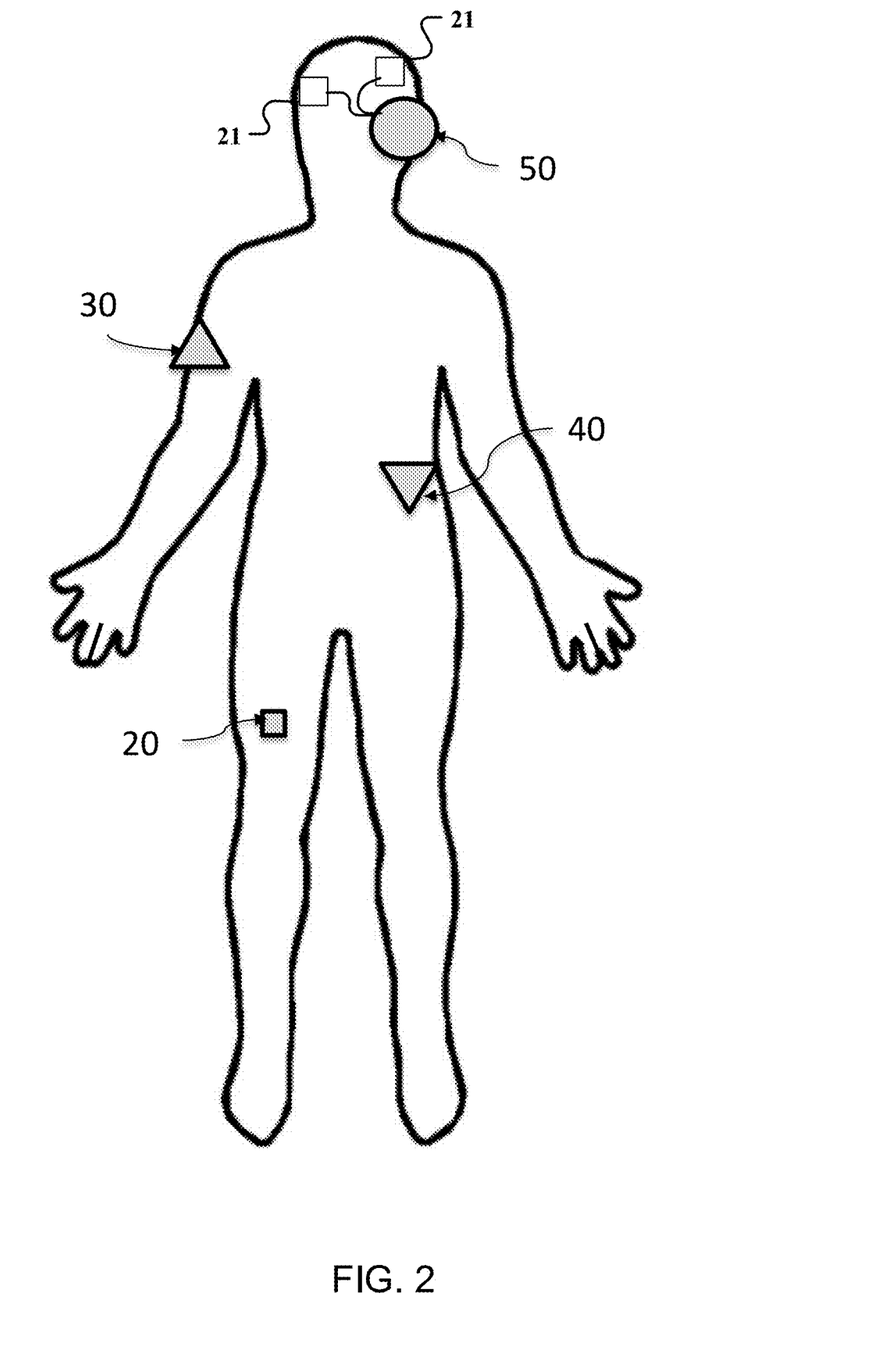
FIG. 2 is a front perspective view of the present invention wherein the signal sensing unit is attached near the muscles of the user and the actuation unit is positioned near the head of the user for exciting the brain with an electrical current, such as with vestibular stimulation or transcranial direct current stimulation.
Figure 3:
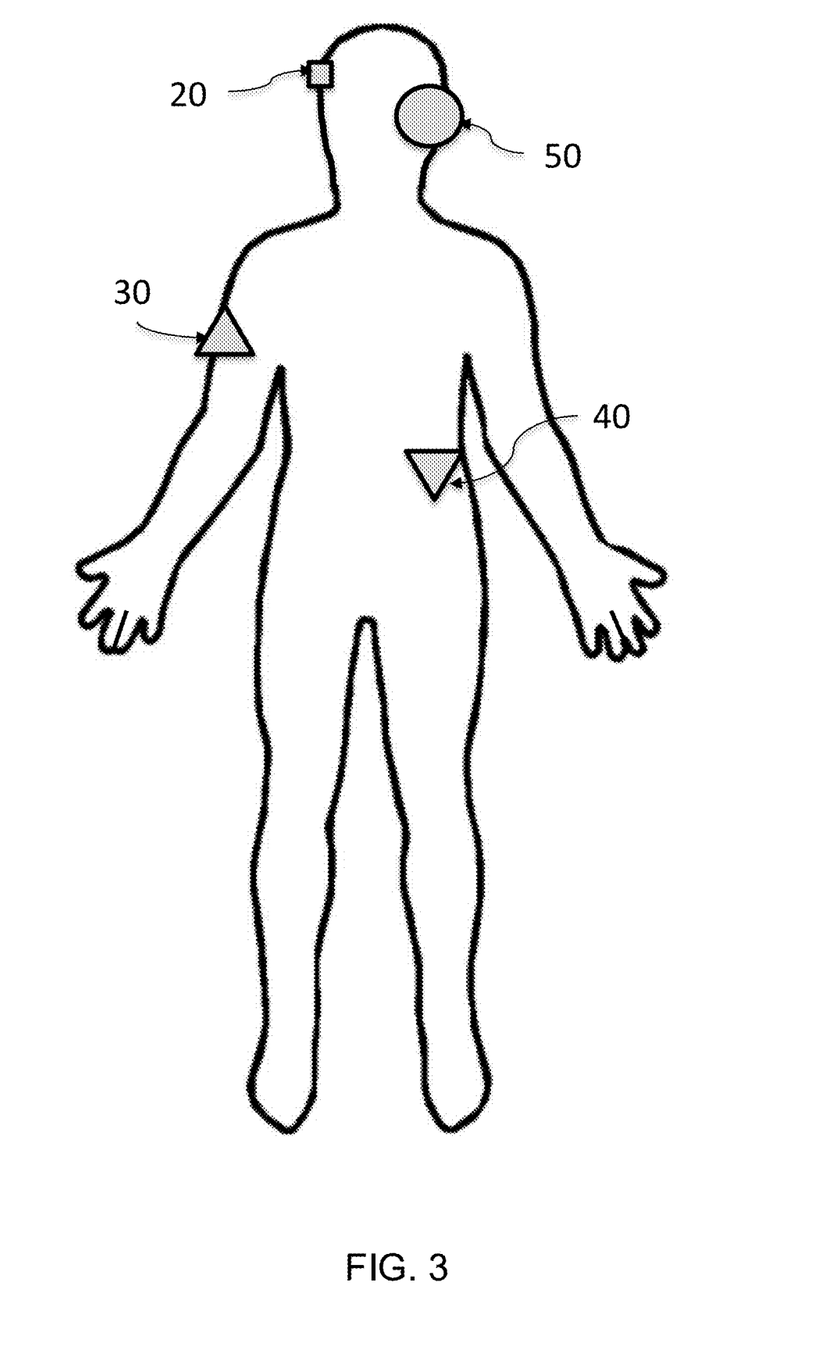
FIG. 3 is a front perspective view of the present invention wherein the signal sensing unit and the actuation unit are positioned near the head of the user for detecting electroencephalographic signals and for exciting the brain with an electrical current.
Figure 4:
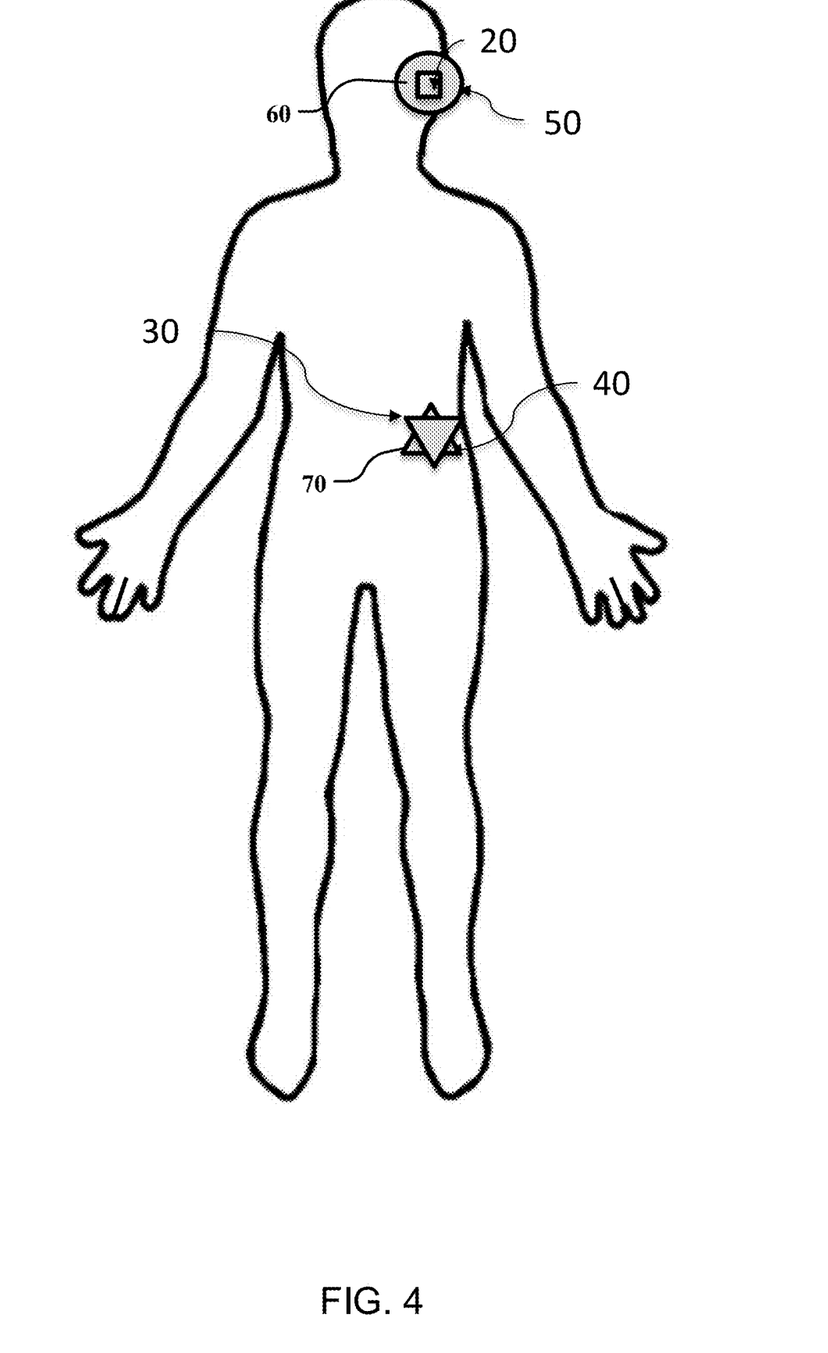
FIG. 4 is a front perspective view of the present invention wherein the signal processing unit and the signal generating unit are combined, and wherein the signal sensing unit and the actuation unit are combined and positioned near the head of the user for brain or vestibular stimulation.
Figure 5:
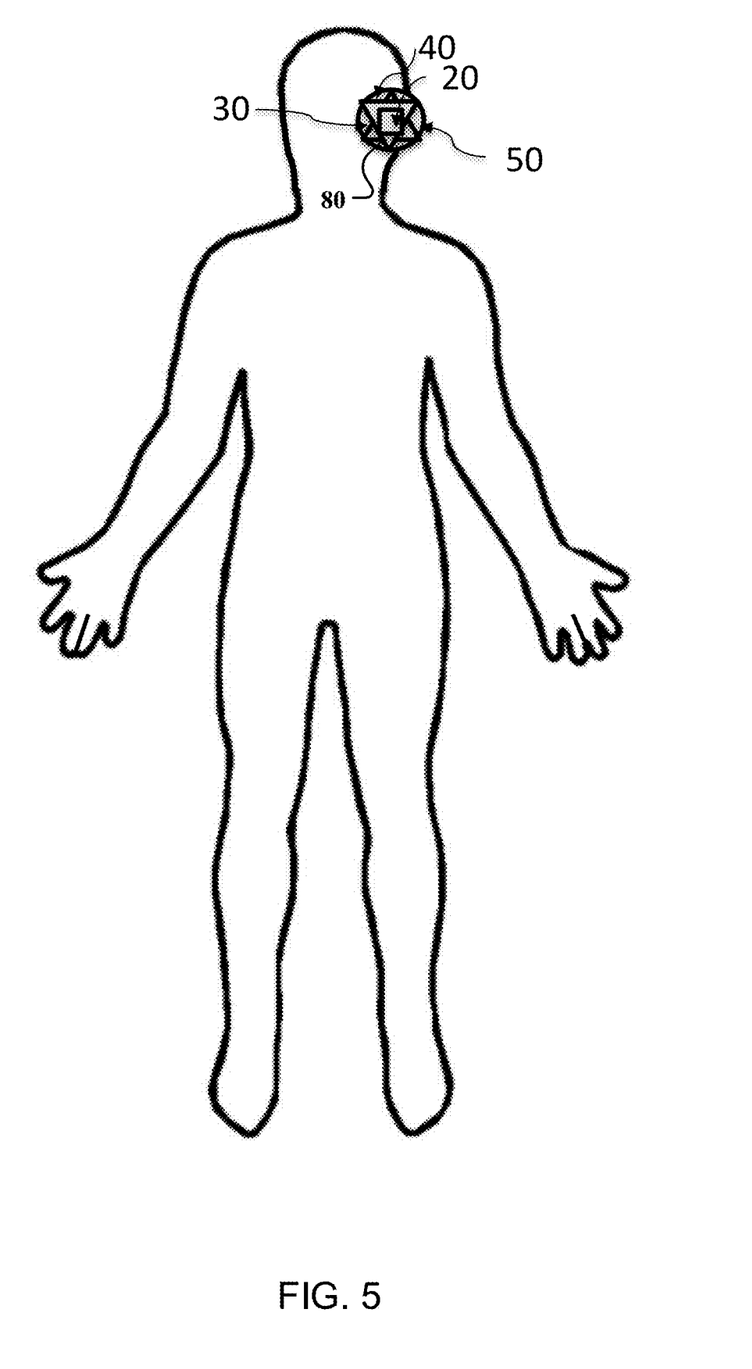
FIG. 5 is a front perspective view of the present invention wherein the signal processing unit, signal generating unit, signal sensing unit, and actuation unit are combined and positioned near the head of the user for detecting and processing neuromuscular signals and accordingly generating and administrating brain or vestibular stimulation.
Figure 6:
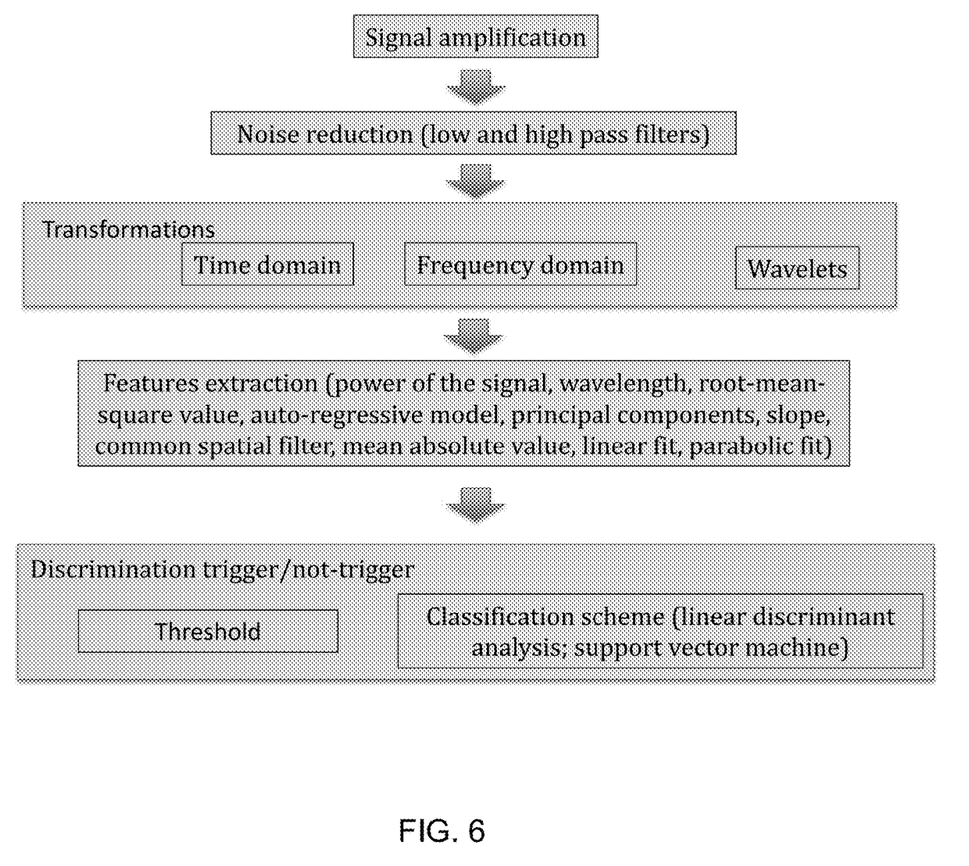
FIG. 6 is a diagram illustrating the process of determining whether a motion-impairing episode is oncoming.
Figure 7:
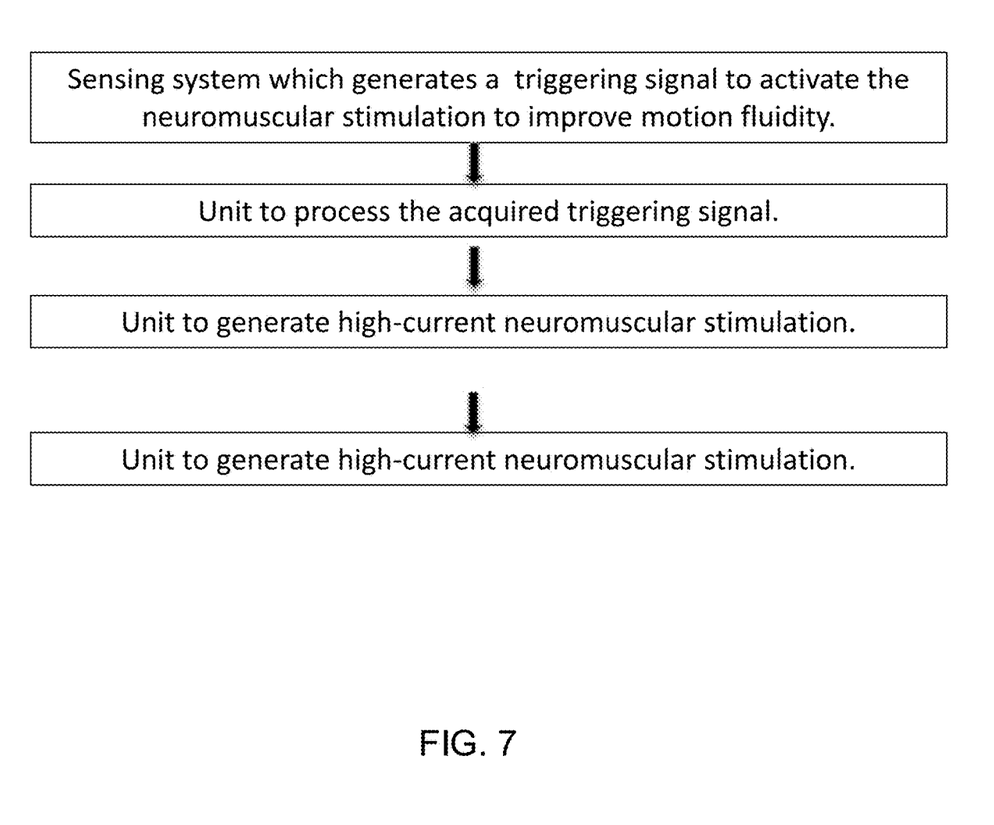
FIG. 7 is a diagram illustrating the process of detecting and unfreezing a user during a movement-impairing episode.
Figure 8:
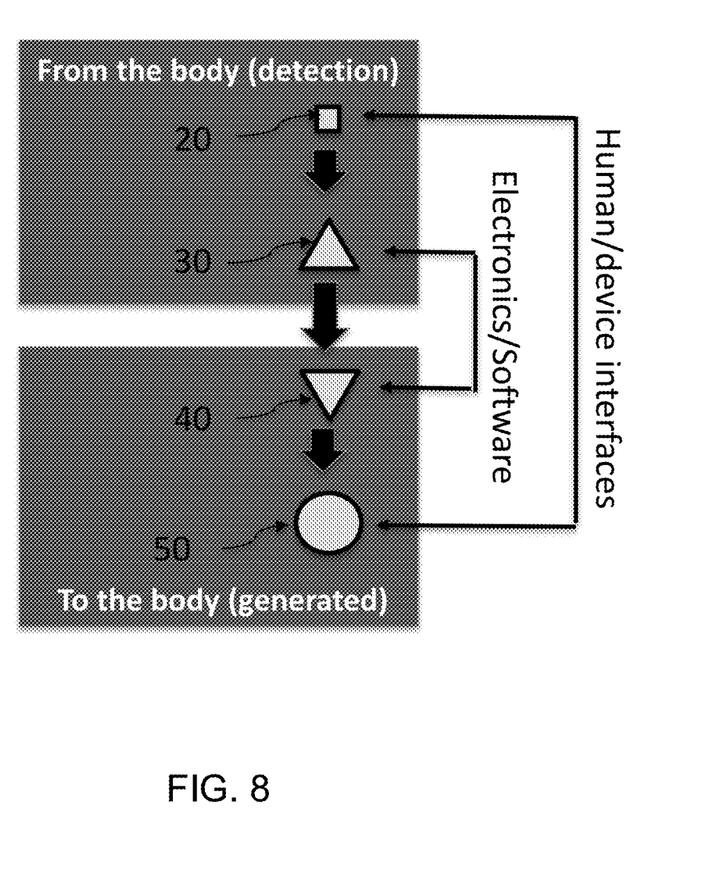
FIG. 8 is a diagram illustrating the components of the present invention.

While the components of the present invention are presented separately, they may be consolidated into one or more units. FIG. 1 illustrates the components as presented above, where the signal sensing unit 20 is attached to the body and is in electrical communication with the signal processing unit 30, the signal generating unit 40, and the actuation unit 50, which is attached to the leg near a muscle. FIG. 2 illustrates an alternative embodiment presented above, where the actuation unit 50 is attached to the head. FIG. 3 illustrates an embodiment where both the signal sensing unit 20 and actuation unit 50 are attached to the head. FIG. 4 illustrates an embodiment where the signal sensing unit 20 and the actuation unit 50 are combined into a detection unit 60 and where the signal processing unit 30 and the signal generating unit 40 are combined into a processing unit 70. An exemplary embodiment of FIG. 4 comprises a pair of earbuds for detecting and sending signals to the user and a cellular phone for signal processing and signal generation. FIG. 5 illustrates an embodiment where all four components are combined into a single unfreezing device 80. An exemplary embodiment of FIG. 4 comprises a pair of earbuds configured to be positioned within the ear canal or behind the ear for both detecting and releasing a movement-impairing episode.

While the above description contains specific details regarding certain elements, sizes, and other teachings, it is understood that embodiments of the invention or any combination of them may be practiced without these specific details. Specifically, although certain signals and configurations are received and applied to certain parts of the body, any suitable location may be used so long as the appropriate information can be sent and received to the patient. These details should not be construed as limitations on the scope of any embodiment, but merely as exemplifications of the presently preferred embodiments. In other instances, well known structures, elements, and techniques have not been shown to clearly explain the details of the invention.

The above detailed description of the embodiments of the invention is not intended to be exhaustive or to limit the invention to the precise form disclosed above or to the particular field of usage mentioned in this disclosure. While specific embodiments of, and examples for, the invention are described above for illustrative purposes, various equivalent modifications are possible within the scope of the invention, as those skilled in the relevant art will recognize. Also, the teachings of the invention provided herein can be applied to other systems, not necessarily the system described above. The elements and acts of the various embodiments described above can be combined to provide further embodiments.

Changes can be made to the invention in light of the above "Detailed Description." While the above description details certain embodiments of the invention and describes the best mode contemplated, no matter how detailed the above appears in text, the invention can be practiced in many ways. Therefore, implementation details may vary considerably while still being encompassed by the invention disclosed herein. As noted above, particular terminology used when describing certain features or aspects of the invention should not be taken to imply that the terminology is being redefined herein to be restricted to any specific characteristics, features, or aspects of the invention with which that terminology is associated.

While certain aspects of the invention are presented below in certain claim forms, the inventor contemplates the various aspects of the invention in any number of claim forms. Accordingly, the inventor reserves the right to add additional claims after filing the application to pursue such additional claim forms for other aspects of the invention.

What is claimed is:

1. An apparatus for detecting and releasing a movement-impairing episode of a user, comprising:
    a signal sensing unit configured to temporarily attach to the body for sensing voluntary and involuntary signals from the user, wherein involuntary signals further comprise signals automatically generated from the user and wherein voluntary signals further comprise signals manually generated from the user;
    a signal processing unit configured to detect electrical fluctuations and process data, said data comprising signal amplification, noise reduction, frequency transformation, wavelet transformation, signal features extraction, signal power, wavelength, root-mean-square value, auto-regressive model, principal components, slope, linear fit, non-linear fit, common special filter, or mean absolute value;
    said signal processing unit configured to compare said data against predefined threshold values or classification or machine learning schemes comprising supervised, unsupervised, semi-supervised, reinforcement, or deep-learning schemes;
    a signal generating unit for generating current signals; and
    an actuation unit configured to temporarily attach to the body for delivering said current signal to the user;
    wherein said signal sensing unit will receive a signal from the user and transduce it into an electrical signal, said signal processing unit will process said electrical signal and calculate whether a movement-impairing episode is oncoming, said signal generating unit will generate an electrical signal current if a movement-impairing episode is detected, and said actuation unit will deliver said electrical signal current to release the user from their movement-impairing episode.

2. The apparatus of claim 1, wherein the actuation unit further comprises one or a plurality of electrodes for delivering current signals to the human body.

3. The apparatus of claim 2, wherein the signal generating unit further comprises generating a current signal for galvanic vestibular stimulation, wherein said electrodes are attached to the head of the user and configured to deliver an electrical current signal to the vestibular system through said electrodes.

4. The apparatus of claim 2, wherein the signal generating unit further comprises generating a current signal for neuromuscular stimulation, wherein said electrodes are attached to the body of the user near a muscle and configured to deliver an electrical current signal to the neuromuscular system through said electrodes.

5. The apparatus of claim 2, wherein the signal generating unit further comprises generating a current signal for neurostimulation, wherein said electrodes are attached to the scalp of the user near and configured to deliver an electrical current signal to the brain through said electrodes.

6. The apparatus of claim 1, wherein the signal sensing unit further comprises one or a plurality of electrodes configured to detect neuromuscular electrical activity.

7. The apparatus of claim 6, wherein the signal processing unit further comprises detecting electrical fluctuations through electroencephalography, wherein said electrodes are attached to the scalp of the user and configured to detect brain activity.

8. The apparatus of claim 6, wherein the signal processing unit further comprises detecting electrical fluctuations through electromyography, wherein said electrodes are attached near a muscle of the user and configured to detect muscle activity.

9. The apparatus of claim 1, wherein voluntary signals further comprise pressing a button, waiving a limb, articulating a voice command, or clenching the teeth.

10. The apparatus of claim 1, wherein the signal sensing unit further comprises detecting movements through inertial measurement units, accelerometers, gyroscopes, and/or magnetometers configured to detect body motion.

11. The apparatus of claim 1, wherein the signal sensing unit and actuation unit are combined into a single detection unit.

12. The apparatus of claim 1, wherein the signal processing unit and signal generating unit are combined into a single processing unit.

13. The apparatus of claim 1, wherein the signal sensing unit, signal processing unit, signal generating unit, and actuation unit are combined into a single device.

14. The apparatus of claim 1, wherein said signal sensing unit and actuation unit are combined into a wearable ear device adapted to detect brain activity and deliver an electrical current signal to the vestibular system.

15. A method for detecting and releasing a movement-impairing episode of a user, comprising:
    detecting voluntary and involuntary signals from the user through a signal sensing unit configured to temporarily attach to the body;
    detecting electrical fluctuations from the user through a signal processing unit;
    processing data, said data comprising signal amplification, noise reduction, frequency transformation, wavelet transformation, signal features extraction, signal power, wavelength, root-mean-square value, auto-regressive model, principal components, slope, linear fit, non-linear fit, common special filter, or mean absolute value;
    comparing said data against predefined threshold values or classification or machine learning schemes comprising supervised, unsupervised, semi-supervised, reinforcement, or deep-learning schemes;
    generating current signals through a signal generating unit; and
    delivering a current signal to the user through an actuation unit configured to temporarily attach to the body;
    wherein said signal sensing unit will receive a signal from the user and transduce it into an electrical signal, said signal processing unit will process said electrical signal and calculate whether a movement-impairing episode is oncoming, said signal generating unit will generate an electrical signal current if a movement-impairing episode is detected, and said actuation unit will deliver said electrical signal current to release the user from their movement-impairing episode.

16. The method of claim 15, wherein said involuntary signals further comprise neuromuscular activity comprising electrical fluctuations beyond a threshold amount.

17. The method of claim 15, wherein said involuntary signals further comprise movements detected through inertial measurement units, accelerometers, gyroscopes, and/or magnetometers configured to detect body motion.

18. The method of claim 15, wherein the signal processing unit further comprises detecting electrical fluctuations through electroencephalography, wherein one or a plurality of electrodes are attached to the scalp of the user and configured to detect brain activity, or wherein the signal processing unit further comprises detecting electrical fluctuations through electromyography, wherein one or a plurality of electrodes are attached near a muscle of the user and configured to detect muscle activity.

19. The method of claim 15, wherein the current stimulation is not provided earlier than 30 minutes before a movement-impairing episode, the current amount does not exceed 3 mA, and the duration does not exceed 60 minutes.

* * * * *